United States Patent [19]

Heyman

[11] Patent Number: 4,624,142

[45] Date of Patent: Nov. 25, 1986

[54] DOUBLE REFERENCE PULSED PHASE LOCKED LOOP

[75] Inventor: Joseph S. Heyman, Williamsburg, Va.

[73] Assignee: The United States of America as represented by the Administrator of the National Aeronautics and Space Administration, Washington, D.C.

[21] Appl. No.: 709,257

[22] Filed: Mar. 7, 1985

[51] Int. Cl.$^4$ .............................................. G01N 29/00
[52] U.S. Cl. ........................................ 73/597; 73/615; 367/99; 356/5
[58] Field of Search ..................... 73/597, 615; 367/99, 367/101; 356/5

[56] References Cited

U.S. PATENT DOCUMENTS

| | | | |
|---|---|---|---|
| 4,014,208 | 3/1977 | Moore et al. | 73/629 |
| 4,079,315 | 3/1978 | Mohr | 324/186 |
| 4,363,242 | 12/1982 | Heyman | 73/579 |
| 4,364,273 | 12/1982 | Redding | 367/101 |
| 4,376,900 | 3/1983 | Metchev | 367/101 |
| 4,402,222 | 9/1983 | Olson et al. | 73/579 |
| 4,453,825 | 6/1984 | Buck et al. | 356/5 |

Primary Examiner—Howard A. Birmiel
Attorney, Agent, or Firm—Howard J. Osborn; John R. Manning; Robert D. Marchant

[57] ABSTRACT

A double reference pulse phase locked loop for measuring the phase shift between tone burst signals initially derived from the same periodic signal source (voltage controlled oscillator 16) and delayed by different amounts because of two different paths. A first path is from transducer 12 to surface 14 of sample 11 and back, and a second path is from transducer 12 to surface 15 and back. A first pulse phase locked loop including phase detector 26 and phase shifter 22 forces the tone burst signals delayed by the second path in phase quadrature with the periodic signal source. A second pulse phase locked loop including phase detector 21 forces the tone burst signals delayed by the first path into phase quadrature with the phase shifted periodic signal source.

12 Claims, 1 Drawing Figure

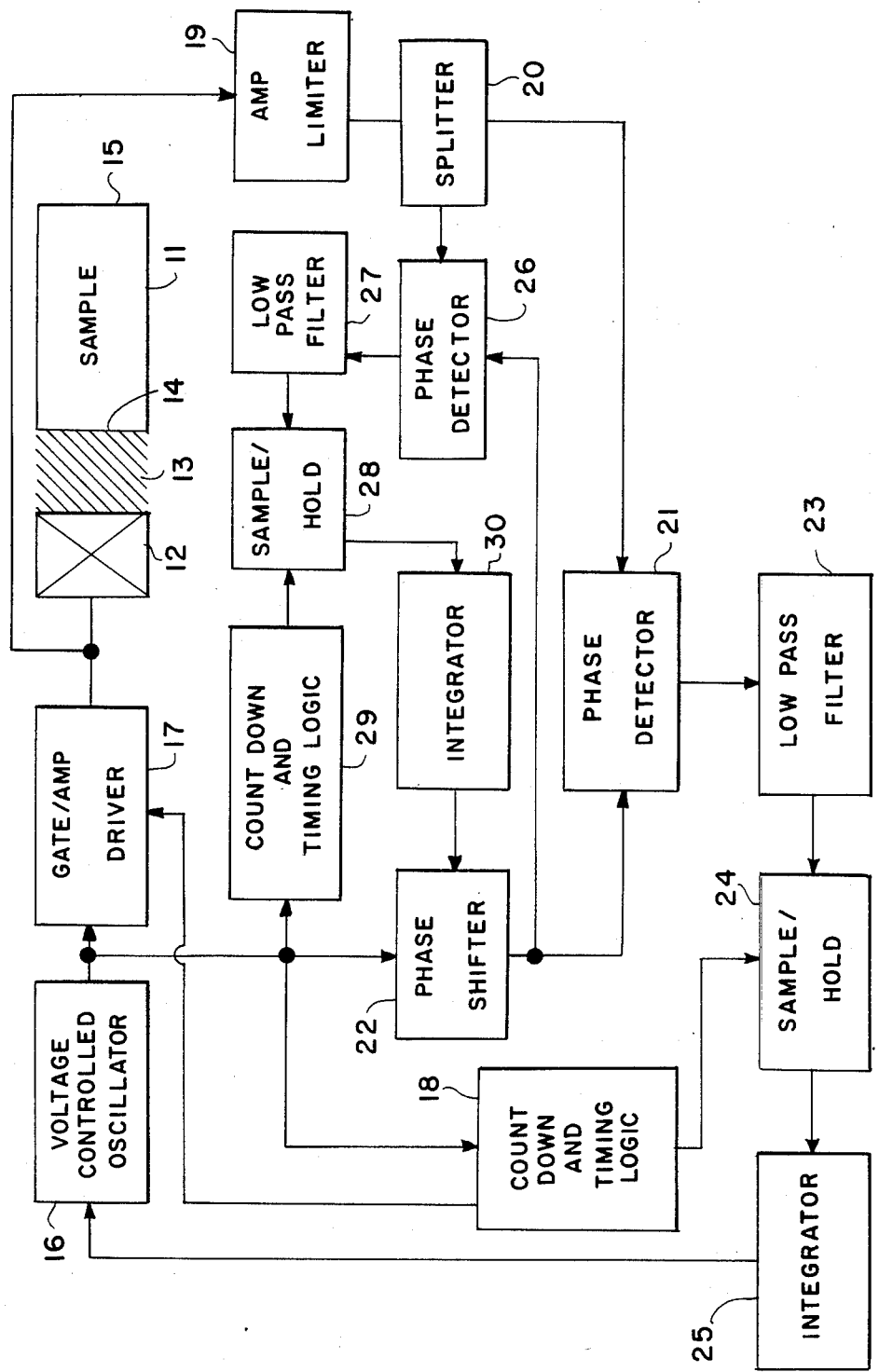

DOUBLE REFERENCE PULSED PHASE LOCKED LOOP

ORIGIN OF THE INVENTION

The invention described herein was made by an employee of the U.S. Government and may be manufactured and used by or for the Government for governmental purposes without the payment of any royalties thereon or therefor.

BACKGROUND OF THE INVENTION

The general purpose of the invention is to allow a precise measurement of phase shift between two tone burst signals initially derived from the same periodic source but delayed by different amounts through either path length differences, propagation velocity differences, or both. For example, the invention can be used to accurately measure the phase shift encountered by an acoustic wave striking the front surface and back surface of a sample. With velocity known, the resulting measurement would be of sample thickness. If thickness is known, the resulting measurement is of sound velocity. Both the above use the relationship $Fm = mV/2l$ where $Fm$ is the harmonic frequency, $m$ the harmonic number (an integer), $V$ the propagation velocity, an $l$ the sample thickness along the propagation direction. The measured parameters are the $Fm$ and the $m$ value. The results apply to all sources of radiation and are not limited to acoustics.

Prior art can be described primarily as pulse timing technology. In general, a delta function or step function pulse of energy is emitted by a source and reflected by a target. This type of measurement is in the time domain. The initial pulse time, $\tau_o$ is used to start a counter and the first reflection, at time $\tau_i$ is used to stop a counter. $\tau_i - \tau_o$ is $\Delta\tau$, the travel time. Sometimes, a second reflector is used at time $\tau_2$ and the measurement consists of $\tau_2 - \tau_1 = \Delta\tau'$. A second type of measurement system exists in the frequency domain. A continuous wave (CW) or pulsed CW source is used to generate a wave. The CW case requires a good sample "geometry" so that standing waves exist. The frequency of resonance is given by $Fm = mV/2l$ while the frequency difference between harmonic is just $\Delta F = V/2L$. For imperfect geometries, a technique uses the discrete sampling of the pulse time domain yet keeps the benefits of the CW phase concepts. This concept, called pulsed phase locked loop ($P^2L^2$), permits accurate measurements of equivalent $\tau_i - \tau_o$ times but in the frequency domain.

The disadvantage of pulse time of flight (TOF) measurements stem from two factors. First a pulse is broadband—i.e. contains many frequency components. Many materials are dispersive—the propagation velocity depends on frequency. This fact clearly flaws the TOF concept. When sample attenuation is included, high frequency energy (fast rise time) is lost preferentially to low frequency (slow rise time) energy. Thus, timing errors occur.

Secondly, a TOF measurement requires setting some signal threshold. This of itself produces an error. The threshold crossing time depends then on signal amplitude. Thus both TOF systems are not pure velocity (or time) concepts. The CW technology requires stringent sample geometry to insure plane waves. The $P^2L^2$ removes that limitation but can only measure $\tau_i - \tau_o$ equivalent times. What is necessary is a measurement system that is narrowband ("single" frequency), independent of signal amplitude over broad ranges, and able to determine $\tau_2 - \tau_i$ or its equivalent by throwing away $\tau_1 - \tau_o$ initialization.

It is an object of this invention to provide precise measurements of phase shift between two tone burst signals initially derived from the same periodic source but delayed by different amounts through either path length differences, propagation velocity differences, or both.

Another object of this invention is to provide precise measurements of the phase shift of radiation between two surfaces where the radiation is derived from a periodic electrical source.

A further object of this invention is to provide precise measurements of phase shifts independent of an unwanted delay caused by path length effects or propagation effects.

Other objects and advantages of this invention will become apparent hereinafter in the specification and drawings.

SUMMARY OF THE INVENTION

The invention utilizes a double reference pulsed phase locked loop to measure the difference in phase shift of pulsed continuous wave radiation traveling along two different paths. The phase shift can be caused by different lengths of the two paths or different materials in the two paths, or both. Pulses of an electrical continuous wave are converted to pulses of radiation which are directed along the two paths. The pulses of radiation are converted back to electrical pulses at the ends of the two paths. The pulses that traveled along one of the paths are forced into phase quadrature with said electrical continuous wave by means of a first pulsed phase locked loop including a voltage controlled phase shifter. The pulses that traveled along the other path are forced into phase quadrature with the output of the phase shifter by means of a second pulsed phase locked loop. Quadrature is obtained in the first loop by varying the phase of the electrical continuous wave and quadrature is obtained in the second loop by varying the frequency of the electrical continuous wave.

BRIEF DESCRIPTION OF THE DRAWING

The sole FIGURE in this application is a block diagram of a preferred embodiment of the invention.

DETAILED DESCRIPTION OF THE INVENTION

Turning now to the embodiment of the invention selected for illustration in the drawing, the number 11 designates a sample whose acoustics characteristics are to be determined. An acoustic transducer 12 is connected acoustically to sample 11 through a layer of water 13. Whenever an electrical signal is applied to transducer 12 an acoustical signal is produced which propagates through the layer of water 13 to sample 11. Part of the energy of the acoustical signal is reflected back to the transducer by the front surface 14 of sample 11 and part of the energy of the acoustical signal is reflected back to the transducer by the back surface 15 of sample 11. That is, the acoustical signal is reflected by both surface 14 and surface 15 with the deflection from surface 15 time delayed with respect to the reflection from surface 14. The purpose of this invention to measure this time delay. The reflections are converted to electrical signals by transducer 12.

A voltage controlled oscillator (VCO) 16 which generates an electrical continuous wave has its output connected to a gate/amplifier driver 17 and a count down and timing logic 18. Logic 18 alternately turns on and turns off gate/amplifier 17. Consequently, several cycles (a pulse) of the electrical continuous wave from VCO 16 is applied to transducer 12, then after a predetermined interval of time a pulse is again applied to transducer 12, and so on. During the intervals of time that the VCO 16 signal is not applied to transducer 12 the two pulsed signals reflected from surfaces 14 and 15 are applied through an amplifier limiter 19 and a splitter 20 to a phase detector 21. The output of VCO 16 is applied through a voltage controlled phase shifter 22 to phase detector 21. The difference in the phases of the two inputs to phase detector 21 is applied through a low pass filter 23 to a sample/hold circuit 24. The count down and timing logic 18 is tuned to apply a signal to sample/hold circuit 24 whenever a reflection from surface 14 is received. Hence sample/hold circuit 24 transfers only the reflections from surface 14 to its output, the reflections from surface 15 are not transferred. An integrator 25 integrates the output from sample/hold circuit 24 and applies the integration to the VCO 16 to control its frequency. The circuitry described above is similar to the prior art pulsed phase locked loop except for the phase shifter 22. However, phase shifter 22 will not interfere with the loop locking. For the loop to lock it is only necessary that the two inputs to phase detector 21 be in phase quadrature-a 90° phase difference between the two inputs. This will be done automatically regardless of the phase shift in the phase shifter 22.

The reflected signals applied to phase detector 21 are also applied to a phase detector 26 by means of splitter 20. The other input to phase detector 26 is from the output of phase shifter 22. The resulting phase signal from phase detector 26 is applied through a low pass filter 27 to a sample/hold circuit 28. A count down and timing logic 29 under the control of VCO 16 is tuned to send a signal to sample/hold circuit 28 to transfer its holding only when the reflected signals from surface 15 are received. The output the sample/hold circuit 28 is integrated by an integrator 30 the output of which controls of the phase of phase shifter 22. This phase loop will automatically lock when the two inputs to phase detector 26 are in phase quadrature.

During the operation of this invention, the loop containing phase detector 21 and the loop containing phase detector 26 are each forced into phase quadrature. Consequently, VCO 16 generates a frequency such that a fixed number M of exact waves (or ½ waves) exists between transducer 12 and surface 14 and a fixed number N of exact waves exists between transducer 12 and surface 15. Hence a fixed number N−M of exact waves exists between surface 14 and surface 15. The same results cannot be obtained using only one loop: even though a fixed number N of exact waves can be guaranteed between surface 15 and transducer 12 there would not necessarily be a fixed number of exact waves between surface 14 and surface 15. The time difference between the two signals reflected from surfaces 14 and 15 is (N−M)1/F where F is the lock frequency and the phase difference between the two signals is (N−M)2π. To make these calculations F can be obtained from the output of VCO 16, and M and N can be obtained from count down and timing logic 18 and 29, respectively.

All of the equipment shown in the drawing, including the count down and timing logic, is well known in the prior art and is therefore not disclosed in detail in this specification.

The advantages of this invention is that it provides a precise measurement of the phase shift between two tone burst signals initially derived from the same source but delayed by different amounts through either path length differences, propagation velocity differences, or both.

It is to be understood that the form of the invention herewith shown and described is to be taken as a preferred embodiment. Various changes can be made without departing from the invention. For example, only two reflecting surfaces are shown, however, any number of reflecting surfaces can exist and the two desired surfaces can be selected by the count down and timing logic. The invention is shown operating in a reflection mode using only one transducer; it is also operable in a transmission mode using two transducers. The invention can use a second VCO at the same frequency as the VCO but in a locked loop to be held in quadrature to the signals reflected by surface 14. The second VCO is then used in place of the phase shifter 22. In addition the invention can use other forms of radiation such as electromagnetic waves - light, radio waves.

Further, the two paths for the propagation of radiation in the preferred embodiment is from transducer 12 to surface 14 and back, and from transducer 12 to surface 15 and back. The two paths could be independent paths such as, for example, through two separate samples in which case the two samples can be compared by determining the difference in phase shift through the two samples.

What is claimed as new and desired to be secured by Letters Patent of the United States is:

1. Method for measuring the phase shift of continuous wave radiation between a first surface and a second surface comprising the steps of:
   generating an electrical continuous wave;
   producing pulses of said electrical continuous wave;
   converting said pulses of said electrical continuous wave into pulses of radiation such that the pulses of radiation will emanate into said first and second surfaces;
   converting the pulses of radiation reflected by said first and second surfaces into reflected electrical pulses;
   phase shifting said generated electrical continuous wave to force it into phase quadrature with the reflected electrical pulses resulting from the reflection from said second surface; and
   varying the frequency of said generated electrical continuous wave to force the phase shifted electrical wave into phase quadrature with the reflected electrical pulses resulting from the reflection from said first surface whereby the phase shift between said first and second surfaces can be determined.

2. Method according to claim 1 wherein said radiation is an acoustic wave.

3. Method for providing precise measurements of phase shift between two time burst signal initially derived from the same periodic electrical source but delayed by different amounts through either path length differences, propagation velocity differences, or both comprising the steps of:
   generating an electrical continuous wave;
   producing pulses of said electrical continuous wave;

converting said pulses of said electrical wave into pulses of radiation;

directing each of said pulses of radiation along a first path and along a second path;

converting said pulses of radiation at the ends of said first and second paths into phase shifted electrical pulses;

phase shifting said generated electrical continuous wave to force it into phase quadrature with the phase shifted electrical pulses that traveled along said second path; and varying the frequency of said generated electrical continuous wave to force the phase shifted generated electrical wave into phase quadrature with the phase shifted electrical pulses that traveled along said first path whereby the difference in phase shift caused by said first and second paths can be determined.

4. Apparatus for measuring the phase shift of continuous wave radiation between a first surface and a second surface comprising:

means for generating an electrical continuous wave;

means for producing pulses of said electrical continuous wave;

means for converting said pulses of said electrical continuous wave into pulses of radiation, for directing said pulses of radiation onto said first and second surfaces and for converting the reflected pulses of radiation into reflected electrical pulses;

means for phase shifting said generated electrical continuous wave to force it into phase quadrature with the reflected electrical pulses resulting from the reflections from said second surface; and means for varying the frequency of said generated electrical continuous wave to force the phase shifted electrical wave into phase quadrature with the reflected electrical pulses resulting from the reflections from said first surface whereby the phase shift between said first and second surfaces can be determined.

5. Apparatus according to claim 4 wherein said means for converting said pulses of said electrical continuous waves into pulses of radiation and for converting the reflected pulses of radiation into reflected electrical pulses is acoustic transducer means.

6. Apparatus according to claim 4 wherein said means for generating an electrical continuous wave is a voltage controlled oscillator.

7. Apparatus according to claim 6 wherein said means for phase shifting said generated electrical continuous wave comprises a pulsed phase locked loop means including a voltage controlled phase shifter for varying the phase shift in said phase shifter to force said electrical continuous wave into phase quadrature with the reflected electrical pulses resulting form the reflections from said second surface.

8. Apparatus according to claim 7 wherein said means for varying the frequency of said generated electrical continuous wave comprises a second pulsed phase locked loop means including said voltage controlled phase shifter for varying the frequency of said voltage controlled oscillator to force the phase shifted electrical wave into phase quadrature with the reflected electrical pulses resulting from the reflections from said first surface.

9. Apparatus according to claim 7 wherein said pulsed phase locked loop means included a count down and timing logic means under the control of said voltage controlled oscillator for selecting the reflected electrical pulses resulting from the reflections from said second surface.

10. Apparatus according to claim 9 wherein said second pulsed phase loop means includes a second count down and timing logic means under the control of said voltage controlled oscillator for selecting the reflected electrical pulses resulting form the reflections from said first surface.

11. Apparatus according to claim 10 wherein said means for producing pulses of said electrical continuous wave is a gating means under the control of said second count downing and timing means.

12. Apparatus for measuring the difference in phase shift of continuous wave radiation when it propagates along a first path and along a second path comprising:

means for generating an electrical continuous wave;

means for producing pulses of said electrical continuous wave;

means for converting said pulses of said electrical continuous wave into pulses of radiation; for directing said pulses of radiation along said first path and along said second path and for converting the pulse of radiation at the end of said first and second paths into phase shifted electrical pulses;

means for phase shifting said generated electrical wave to force it into phase quadrature with the phase shifted electrical pulses that traveled along said first path; and means for varying the frequency of said generated electrical continuous wave to force the phase shifted said generated electrical wave into phase quadrature with the phase shifted electrical pulses that traveled along said second path whereby the phase shift difference between the first and second paths can be determined.

* * * * *